(12) United States Patent
Edwards

(10) Patent No.: US 6,409,723 B1
(45) Date of Patent: *Jun. 25, 2002

(54) TREATING BODY TISSUE BY APPLYING ENERGY AND SUBSTANCES

(75) Inventor: Stuart D. Edwards, 658 Westridge Dr., Portola Valley, CA (US) 94028

(73) Assignee: Stuart D. Edwards, Portola Valley, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,575
(22) Filed: Apr. 2, 1999
(51) Int. Cl.[7] .............................................. A61B 18/18
(52) U.S. Cl. ................................ 606/41; 606/14; 606/2; 607/101; 607/104; 607/105; 607/80; 604/20; 604/21; 604/96.01; 604/506
(58) Field of Search ........................... 606/2, 3, 13–16, 606/33–40, 41; 607/2, 3, 88–94, 100, 101; 514/63; 604/20, 21, 96

(56) References Cited

U.S. PATENT DOCUMENTS

| | | | | |
|---|---|---|---|---|
| 5,405,369 A | * | 4/1995 | Selman et al. | 607/88 |
| 5,454,807 A | * | 10/1995 | Lennox et al. | 606/15 |
| 5,514,669 A | * | 5/1996 | Selman | 514/63 |
| 5,609,591 A | * | 3/1997 | Daikuzono | 606/15 |
| 5,709,653 A | * | 1/1998 | Leone | 604/20 |
| 5,766,234 A | * | 6/1998 | Chen et al. | 607/92 |
| 5,964,755 A | * | 10/1999 | Edwards | 606/41 |
| 6,013,053 A | * | 1/2000 | Bower et al. | 604/96 |
| 6,027,499 A | * | 2/2000 | Johnston et al. | 606/22 |
| 6,077,257 A | * | 6/2000 | Edwards et al. | 604/506 |
| 6,159,236 A | * | 12/2000 | Biel | 607/92 |
| 6,273,886 B1 | | 8/2001 | Edwards et al. | 606/34 |
| 6,325,789 B1 | | 12/2001 | Edwards et al. | 606/41 |

* cited by examiner

Primary Examiner—Linda C. M. Dvorak
Assistant Examiner—Ahmed Farah
(74) Attorney, Agent, or Firm—Michael A. Glenn (57) ABSTRACT

A method and apparatus for treatment for body structures, especially internal body structures involving disorders involving unwanted features or other disorders, that does not require relatively invasive surgery, and is not subject to other drawbacks noted with regard to the known art. A relatively minimally invasive catheter is inserted into the body, treatment of the body structures is applied using the catheter, and the unwanted features or disorders are relatively cured using the applied treatments. The applied treatments can include application of energy or substances, including application of energy (such as of radio frequency energy, microwave energy, or laser or other electromagnetic energy) or substances (such as collagen or other bulking, plumping, or shaping agents; saline or other energy-receiving electrolytes; astringents or other debulking, reducing, or shaping agents; antibiotics or other bioactive, chemoactive, or radioactive compounds). More than one applied treatment can be performed, either in conjunction, in parallel, or seriatim, so as to achieve a combined effect more substantial than any one individual such applied treatment.

18 Claims, 5 Drawing Sheets

TREATING BODY TISSUE BY APPLYING ENERGY AND SUBSTANCES

RELATED APPLICATIONS

Inventions described herein can be used in combination or conjunction with inventions described in the following patent application(s):

application Ser. No. 08/731,372, filed Oct. 11, 1996, now U.S. Pat. No. 5,964,775, claiming priority dates at least as early as Jun. 24, 1994, in the name of Stuart D. Edwards, and all pending cases claiming priority thereof;

application Ser. No. 09/026,316, filed Feb. 19, 1998, now U.S. Pat. No. 6,056,744, in the name of Stuart D. Edwards, and all pending cases claiming priority thereof;

application Ser. No. 08/677,811, filed Jul. 10, 1996, now U.S. Pat. No. 5,921,954, in the name of Lawrence J. Mohr, Jr., and Stuart D. Edwards, titled "Treating Aneurisms by Applying Hardening/Softening Agents to Hardenable/Softenable Substances," and all pending cases claiming priority thereof;

application Ser. No. 08/717,612, filed Sep. 20, 1996, now U.S. Pat. No. 6,077,257, in the name of Stuart D. Edwards and Steven Marcus, titled "Ablation of Rectal and Other Internal Body Structures," assigned to the same assignee, and all pending cases claiming priority thereof; and application Ser. No. 08/795,656, filed Feb. 6, 1997, in the name of Stuart D. Edwards and Muta M. Issa, titled "Treating Urinary and Other Body Structures," assigned to the same assignee, and all pending cases claiming priority thereof.

These applications are each hereby incorporated by reference as if fully set forth herein. These applications are collectively referred to herein as "Incorporated Disclosures."

BACKGROUND OF THE INVENTION

1. Field of the Invention

This invention relates to treating body tissue, particularly to treating body tissue by altering the shape or volume of that body tissue using energy or substances deployed from an interstitial location in the body.

2. Related Art

Human beings are subject to a number of medical disorders, including those in which a body structure is subject to unwanted features or is otherwise dysfunctional. The body structure can for example include muscular tissue, mucosal tissue, gastro-intestinal tissue, lumen walls, stenotic locations in lumens or interstitial locations, or tumors or other cancerous or precancerous conditions. The unwanted features can for example include being distended or engorged, being unduly large or small, being misshapen, having cysts or tumors, or having undesirable growths. Other dysfunctions can include aneurysms, diverticuli, fissures, hemorrhoids, tumors, or simply an inability for the body structure to perform its proper function.

Medical disorders of these kinds can be particularly acute or discomfiting when they involve important areas of the body, including the cardiovascular system, the gastro-intestinal tract, the genito-urinary system, the pulmonary system, the vascular system, or other body systems. For a first example, disorders involving body structures in the gastro-intestinal tract can lead (at a first end thereof) to inadequate operation of the esophageal sphincter, to gastro-intestinal reflux, or to Barrett's condition. For a second example, disorders involving body structures in the gastro-intestinal tract can lead (at a second end thereof) to fecal or urinary incontinence.

One problem in the known art is that treatment of such disorders can involve relatively invasive and labor-intensive surgery. This has the drawbacks of incurring relatively high expense, of incurring relatively high risk (in some cases) of damage to important nerves, and of producing iatrogenic effects that are relatively hazardous to the patient.

Accordingly, it would be advantageous to provide a method and apparatus for treatment for body structures, especially internal body structures involving unwanted features or other disorders, that does not require relatively invasive surgery, and is not subject to other drawbacks noted with regard to the known art. This advantage is achieved in an embodiment of the invention in which a relatively minimally invasive catheter is inserted into the body, treatment of the body structures is applied using the catheter, and the unwanted features or disorders are relatively cured using the applied treatments. The applied treatments can include application of energy or substances, including application of energy (such as of radio frequency energy, microwave energy, or laser or other electromagnetic energy) or substances (such as collagen or other bulking, plumping, or shaping agents; saline or other energy-receiving electrolytes; astringents or other debulking, reducing, or shaping agents; antibiotics or other bioactive, chemoactive, or radioactive compounds). More than one applied treatment can be performed, either in conjunction, in parallel, or seriatim, so as to achieve a combined effect more substantial than any one individual such applied treatment.

SUMMARY OF THE INVENTION

The invention provides a method and system for treatment for body structures, especially internal body structures involving unwanted features or other disorders, that does not require relatively invasive surgery, and is not subject to other drawbacks noted with regard to the known art. A relatively minimally invasive catheter is inserted into the body, treatment of the body structures is applied using the catheter, and the unwanted features or disorders are relatively cured using the applied treatments.

In a preferred embodiment, the applied treatments can include application of energy or substances, including application of energy (such as of radio frequency energy, microwave energy, or laser or other electromagnetic energy) or substances (such as collagen or other bulking, plumping, or shaping agents; saline or other energy-receiving electrolytes; astringents or other debulking, reducing, or shaping agents; antibiotics or other bioactive, chemoactive, or radioactive compounds).

In a preferred embodiment, more than one applied treatment can be performed, either in conjunction, in parallel, or seriatim, so as to achieve a combined effect more substantial than any one individual such applied treatment.

In preferred embodiments, the unwanted features or other disorders include one or more of the following:

Barrett's disease, other growths on the esophageal lining or near the esophageal sphincter, or otherwise at an ingestive end of the gastro-intestinal system;

fecal incontinence or other failures of the musculature or sphincters at an excretory end of the gastro-intestinal system; or urinary incontinence or other failures of the musculature or sphincters at an excretory end of the gastro-intestinal system.

DETAILED DESCRIPTION OF THE PREFERRED EMBODIMENT

In the following description, a preferred embodiment of the invention is described with regard to preferred process steps and data structures. Those skilled in the art would recognize after perusal of this application that embodiments of the invention can be implemented using processors or circuits adapted to particular process steps and data structures described herein, and that implementation of the process steps and data structures described herein would not require undue experimentation or further invention.

First Treatment Device

Figure 1:
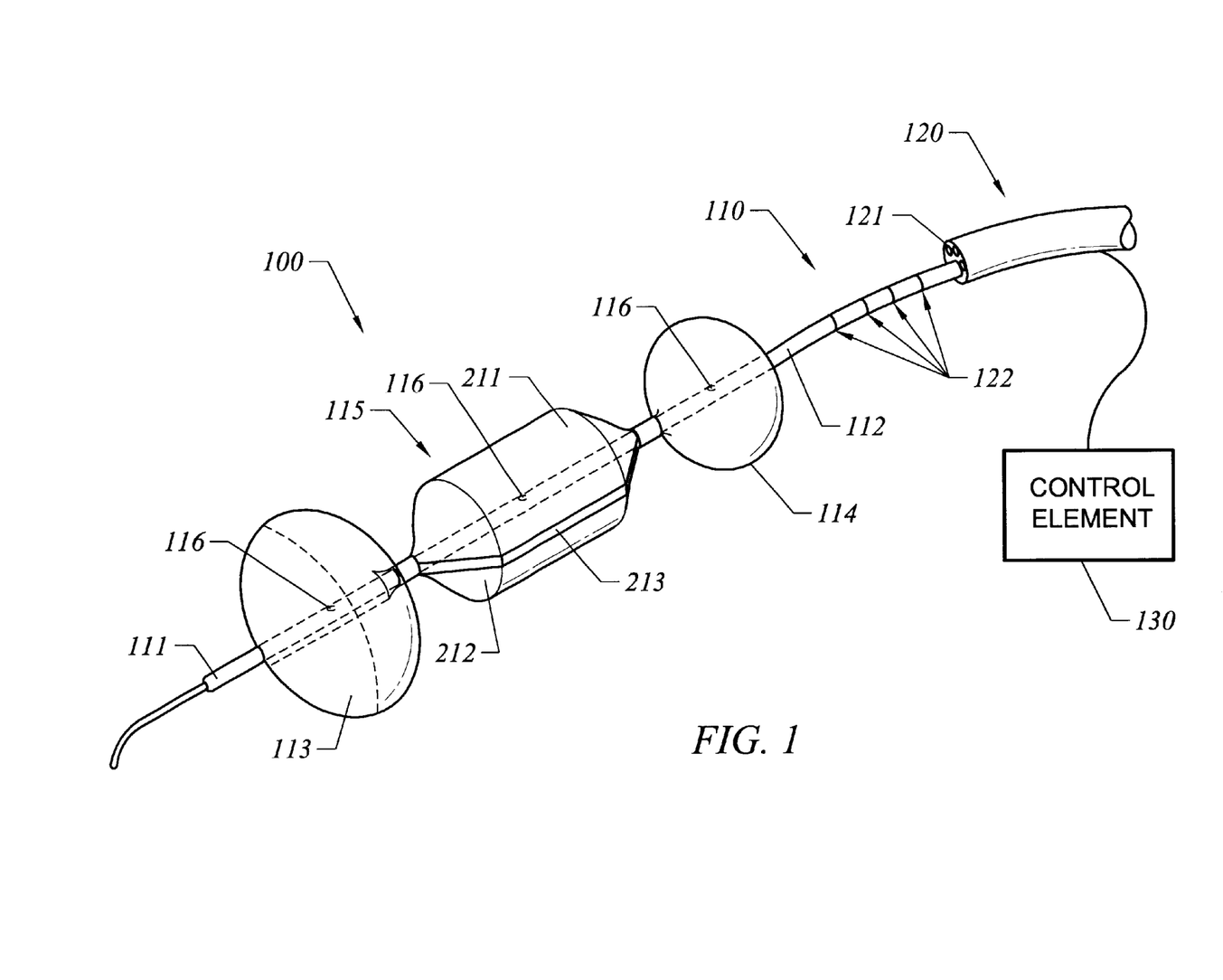
FIG. 1 shows a drawing of a first device for treatment of a body structure, for possible application to body structures at an ingestive end of the gastro-intestinal system.

FIG. 1 shows a drawing of a first device for treatment of a body structure, for possible application to body structures at an ingestive end of the gastro-intestinal system.

A device 100 includes a catheter 110, the catheter 110 having a distal end 111, a proximal end 112, a distal balloon 113, a proximal balloon 114, a treatment structure 115, and a set of aspiration or delivery elements 116.

The distal end 111 is disposed for insertion into a cavity of the body. In a preferred embodiment, the cavity can include a section of the gastro-intestinal tract of the body. In alternative embodiments, the cavity may include one or more of, or some combination of, the following.

Any portion of the bronchial system, the cardiovascular system, the genito-urinary tract, the lymphatic system, the pulmonary system, the vascular system, or other systems in the body;

Any biologic conduit or tube, such as a biologic lumen that is patent or one that is subject to a stricture;

Any biologic cavity or space, such as a cyst, a gland, a layered structure or striation, or a medical device implanted or inserted in the body;

Any biologic operational structure, such as a gland, or a muscular or other organ (such as the colon, the diaphragm, the heart, a kidney, a lung, the rectum, an involuntary or voluntary sphincter);

Any other biologic structure, such as a herniated body structure, a set of diseased cells, a set of displaisic cells, a surface of a body structure (such as the sclera), a tumor, or a layer of cells (such as fat, muscle, or skin).

The proximal end 112 is disposed for coupling to a medical device 120. In a preferred embodiment, the medical device 120 can include a device for insertion and probing into the body, such as a colonoscope, an endoscope, or another type of catheter. The medical device 120 is preferably controlled from a location outside the body, such as an instrument in an operating room or an external device for manipulating the inserted catheter 110.

For example, in a preferred embodiment in which the medical device 120 includes an endoscope, the device 110 can be coupled to one of a plurality of lumens 121 in the medical device 120 for sensing, for delivery or aspiration of substances, or for delivery of energy. For example, one or more of the lumens 121 can include an optical wave-guide, a delivery path for antibiotics or saline, an aspiration path for liquids or killed cells, or a delivery path for electromagnetic energy.

In alternative embodiments, the medical device 120 may include a device that is implanted into the body, or is inserted into the body and manipulated from inside or outside the body during a medical procedure. For example, the medical device 120 can include a programmed AICD (artificial implanted cardiac defibrillator), a programmed glandular substitute (such as an artificial pancreas), or a medical device 120 for use during surgery or in conjunction with other medical procedures.

In a preferred embodiment, the medical device 120 is coupled to a control element 130, by which medical or other personnel can control operation of the medical device 120, and of the catheter 110. Such control can include aspiration or delivery of substances, or delivery or sensing of energy.

The distal balloon 113 is disposed for inflation, preferably after the catheter 110 has been inserted into the body. The distal balloon 113 can be disposed with regard to the catheter 110 in conjunction with marlings 121 on or near the proximal end 112, so that medical or other personnel can determine a distance the distal end 111 has penetrated within the body. For example, in a preferred embodiment in which the in which the catheter 110 is inserted into the rectum for treatment of incontinence, the markings 121 can be used to determine that distance.

The inflated distal balloon 113 can perform one or more of, or some combination of, the following functions:

The distal balloon 113 can position the catheter 110 in a relatively fixed position within the body. For example, in a preferred embodiment in which the catheter 110 is inserted into the urethra, the inflated distal balloon 113 can prevent the catheter 110 from being pulled back out of the urethral canal.

The distal balloon 113 can isolate the catheter 110 (and its treatment structure 115) from the rest of the body. For example, in a preferred embodiment in which the catheter 110 is inserted into the rectum, the inflated distal balloon 113 can prevent treatment substances and any substances that result from treatment (such as killed cells) from passing into other regions of the body.

The distal balloon 113 can serve as a sensor. For example, the distal balloon 113 can include an x-ray opaque element or an x-ray reflector, so as to enable medical or other personnel to determine a position of the catheter 110 using a fluoroscope or an x-ray device.

The distal balloon 113 can serve as a delivery element for electromagnetic energy. For example, the distal balloon 113 can include a set of metallic (or metallic coated) elements, or can be coupled to a basket having a set of electrodes, for delivery of RF or other electromagnetic energy.

In a preferred embodiment in which the distal balloon 113 is used as a delivery element for electromagnetic energy, the distal balloon 113 is spherical (or ellipsoidal) and conceptually divided into a set of eight octants (each preferably a semidemihemisphere). Each octant can be separately activated to deliver electromagnetic energy to selected body structures near the distal balloon 113.

In a preferred embodiment in which the distal balloon 113 is used as a delivery element for electromagnetic energy, the distal balloon 113 includes a microporous or otherwise partially porous membrane, so that saline or another substance can be exuded from the distal balloon 113. The saline or other substance are preferably used to pre-condition tissue for reception of the electromagnetic energy, or to receive that electromagnetic energy itself. For example, in a preferred embodiment, the distal balloon 113 exudes about 10% saline and delivers about 460 kilohertz RF energy using the saline as a receiving antenna.

Delivery of RF or other electromagnetic energy is described in further detail herein below.

Similarly, the proximal balloon 114 is also disposed for inflation. The proximal balloon 114 can also be disposed with regard to the catheter 110 in conjunction with markings 121 on or near the proximal end 112, so that medical or other personnel can determine a distance the distal end 111 has penetrated within the body.

Similarly, the inflated proximal balloon 114 can perform one or more of, or some combination of, the following functions:

The proximal balloon 114 can position the catheter 110 in a relatively fixed position within the body. For example, in a preferred embodiment in which the catheter 110 is inserted into the urethra, the inflated proximal balloon 114 can prevent the catheter 110 from being inserted further into the urethral canal.

The proximal balloon 114 can isolate the catheter 110 (and its treatment structure 115) from the rest of the body. For example, in a preferred embodiment in which the catheter 110 is inserted into the esophagus, the inflated proximal balloon 114 can prevent treatment substances and any substances that result from treatment (such as killed cells) from passing into other regions of the body.

The proximal balloon 114 can serve as a sensor. For example, the proximal balloon 114 can include an x-ray opaque element or an x-ray reflector, so as to enable medical or other personnel to determine a position of the catheter 110 using a fluoroscope or an x-ray device.

The proximal balloon 114 can serve as a delivery element for electromagnetic energy. For example, the proximal balloon 114 can include a set of metallic (or metallic coated) elements, or can be coupled to a basket having a set of electrodes, for delivery of RF or other electromagnetic energy.

The treatment structure 115 includes a shaped balloon, having a cylindrical shape with an indentation, and having a treatment element disposed in the indentation. The treatment structure 115 is further described with regard to FIG. 2.

The aspiration or delivery elements 116 include a set of holes or other passages, through which substances can be exuded or flowed. For aspiration, the aspiration or delivery elements 116 can be coupled to a pump or other suction element, so as to generate suction to drain flowable material from the body. For delivery, the aspiration or delivery elements 116 can be coupled to a pump or other pressure element, and to a source of flowable substances, so as to generate pressure to source flowable material into the body.

Treatment Device Used for Esophagus

Figure 2:
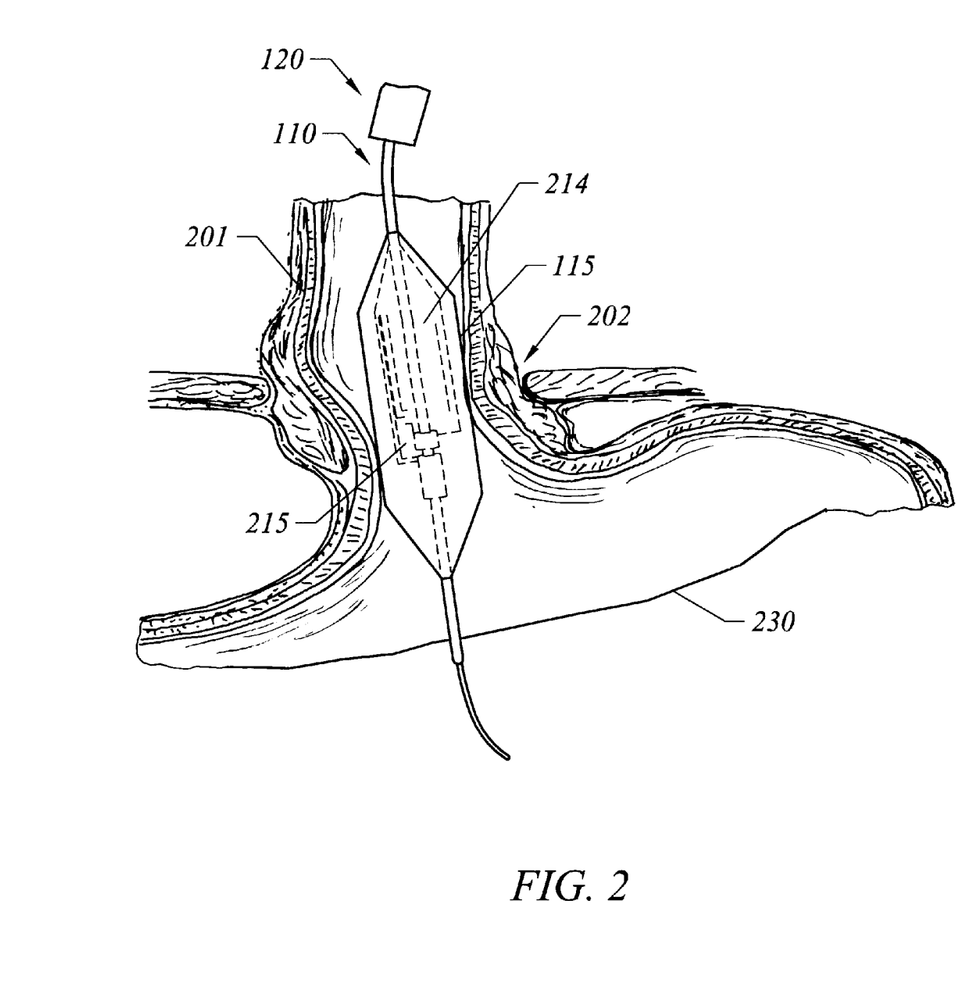
FIG. 2 shows a drawing of the first device for treatment of a body structure, as possibly positioned at or near an esophageal sphincter.

FIG. 2 shows a drawing of the first device for treatment of a body structure, as possibly positioned at or near an esophageal sphincter.

The catheter 110 is inserted into the body and disposed so that the treatment structure 115 is located at or near a region between the esophagus 201 and an esophageal sphincter 202 (between the esophagus 201 to the stomach 203).

The treatment structure 115 includes a shaped balloon 211, having a cylindrical shape with an indentation 212, and having a treatment element 213 disposed in the indentation 212.

Disposed in the body, the shaped balloon 211 substantially fills the region of the esophagus 201 near the esophageal sphincter 202. The shaped balloon 211 thus isolates a mucosal surface of the esophagus 201 from treatment, except for a region defined by the indentation 212.

The region defined by the indentation 212 includes a portion of the mucosal surface area of the esophagus 201, which portion is selected for treatment. In an embodiment used to treat Barrett's, a portion is selected for treatment that has cells foreign to a normal esophagus 201 (such as cells like those of the stomach lining, displaisic cells, or pre-cancerous cells). In a preferred embodiment, the portion selected for treatment includes no more than a 90-degree arc of a cross-section of the esophagus 201, and preferably no more than a 45-degree arc. The indentation 212 is no more than 90 degrees of arc, and preferably no more than 45 degrees of arc.

The treatment element 213 includes a set of treatment points 214, each coupled using a separate controller 215 to the medical device 120 or to the control element 130. In a preferred embodiment, each treatment point 214 can be separately controlled using the control element 130 so as to select a variable length portion of the esophagus 201 for treatment.

The indentation 212 and the treatment element 213 can be rotated with the device 100 so as to select a second portion of the mucosal surface area of the esophagus 201 for treatment. In a preferred embodiment, the second portion of the mucosal surface area of the esophagus 201 is selected only after a first portion of the mucosal surface area of the esophagus 201 has been treated and given time to heal.

The treatment points 214 each include unipolar RF (radio frequency) electrodes, each of which can operate to treat tissue by ablation, cell death, desiccation, or other aspects of delivery of RF energy to tissue. In a preferred embodiment, the shaped balloon 211 can be expanded and filled using relatively cold saline, so that the surface of the esophagus 201 isolated by the shaped balloon 211 can be kept at a relatively lower temperature during treatment.

In alternative embodiments, the treatment points 214 can be disposed to treat tissue using other techniques, such as by emission of other forms of energy or by emission of substances. These can include one or more of, or some combination of, any of the following:

bipolar RF electrodes;

chemical treatment, such as acid, antibiotics, enzymes, or other bioactive, chemoactive, or radioactive substances;

heat, such as using heated saline or other heated substances;

infrared energy, such as from an infrared laser or a diode laser;

microwave energy, such as electromagnetic energy in the about 915 megahertz to about 2.45 gigahertz range;

optical energy, such as from a laser;

other electromagnetic energy, including direct current or ELF (extremely low frequency);

physical treatment, such as crushing using an expandable balloon, scraping using an attachment to an expandable balloon, or another physical treatment technique; or sonic energy, including ultrasound.

In a preferred embodiment, the treatment points 214 can also be disposed to pre-condition or pre-treat tissue so as to be conditioned, sensitized, or otherwise prepared for treatment. In a preferred embodiment, the pre-treatment includes exuding saline for absorption into the treated tissue. The absorbed saline acts to enhance reception of electromagnetic (particularly RF) energy by the tissue.

In alternative embodiments, the treatment points 214 can be disposed to pre-condition or pre-treat tissue using other techniques, such as by emission of other forms of energy or by emission of other substances. These can include any of the forms of energy or substances used for treatment, and can also include one or more of, or some combination of, any of the following:

- a bulking, plumping, or supportive agent, such as a collagen, a gel, or a stent;
- a debulking, deplumping, or astringent or restrictive agent, such as an acid, an enzyme, or a physical constraint such as an elastic or wire; or
- a shaping or reshaping agent, such as a cutting element or a stent.

In a preferred embodiment, the treatment points 214 can also be disposed to post-condition or post-treat tissue so as to be healed or otherwise repaired after treatment. In a preferred embodiment, the post-treatment includes exuding analgesic, antibiotic, or anti-inflammatory agents, for absorption into the treated tissue, and tissue nearby. The post-treatment acts to enhance the ability of the treated tissue, and tissue nearby, to recover from treatment.

In alternative embodiments, the treatment points 214 can be disposed to post-condition or post-treat tissue using other techniques, such as by emission of other forms of energy or by emission of other substances.

Second Treatment Device

Figure 3:
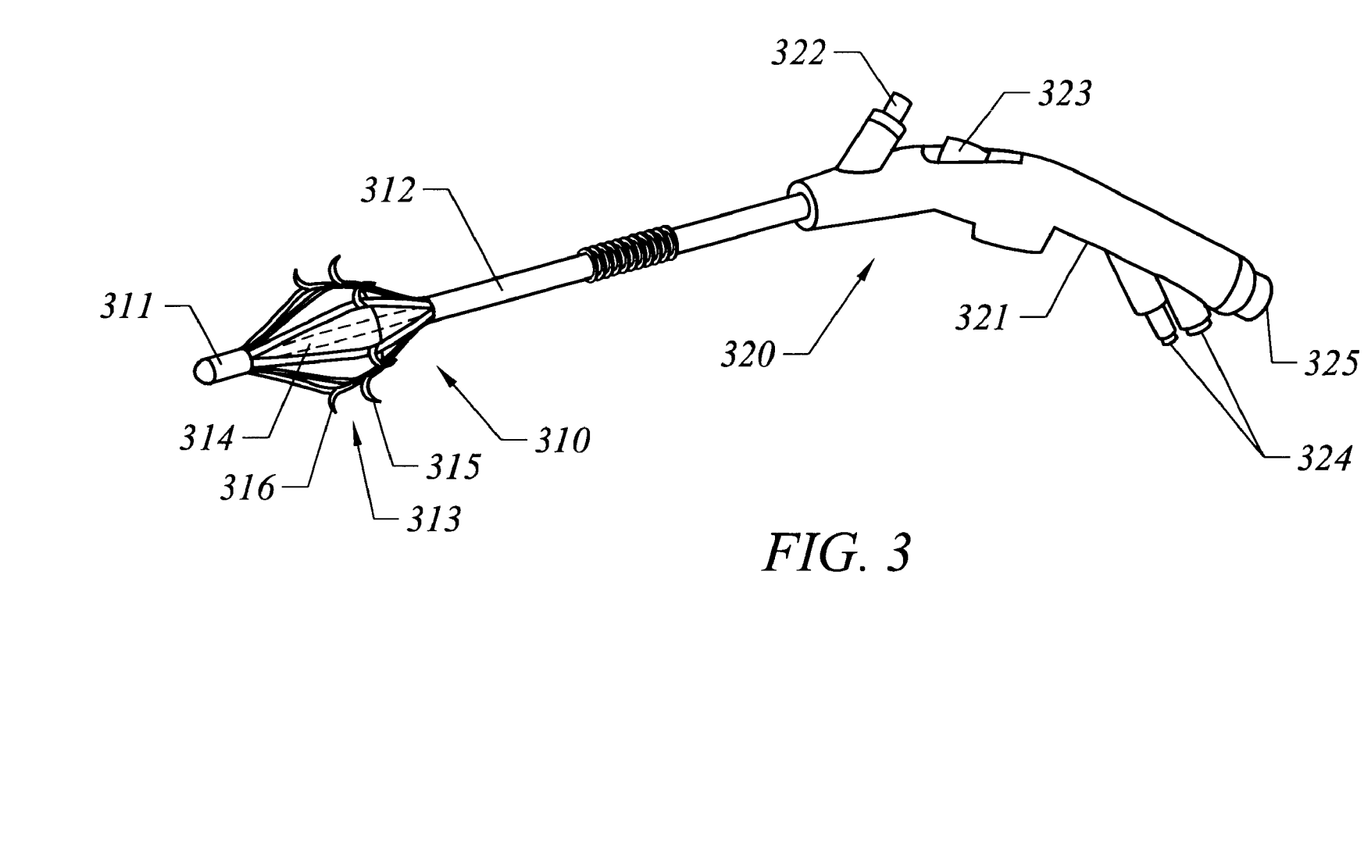
FIG. 3 shows a drawing of a second device for treatment of a body structure, for possible application to body structures at an excretory end of the gastro-intestinal system.

FIG. 3 shows a drawing of a second device for treatment of a body structure, for possible application to body structures at an excretory end of the gastro-intestinal system.

A device 300 includes a catheter 310 and a control element 320.

The catheter 310 includes a distal end 311, a proximal end 312, and a treatment structure 313.

The distal end 311 and the proximal end 312 of the catheter are similar to the distal end 111 and proximal end 112 described with regard to FIG. 1.

The treatment structure 313 includes an inflatable/deflatable structure 314, a set of treatment elements 315, and a set of treatment element extrusion ports 316.

The inflatable/deflatable structure 314 includes a balloon disposed within a flexible basket, so that when the balloon is inflated or deflated, the flexible basket is expanded or contracted. In a preferred embodiment, the balloon is at least partially microporous or porous, so that flowable substances used to expand or fill the balloon can be exuded from the balloon into surrounding tissue.

The treatment elements 315 include electrodes, physically coupled to the control element 320, and disposed for extrusion using the treatment element extrusion ports 316.

The treatment element extrusion ports 316 include holes or other passageways in the flexible basket, so the electrodes can be extruded therethrough.

The electrodes are substantially curved, so that in a non-extruded state the electrodes are disposed within the flexible basket, and that in an extruded state the electrodes are disposed outside the flexible basket at a substantial angle to the direction at which the electrodes are extruded. The electrodes preferably have sufficient length and curve so that the substantial angle exceeds about 60 degrees of arc, and can exceed 180 degrees of arc from the direction at which the electrodes are extruded.

The control element 320 includes a handle 321, an inflation/deflation port 322, an electrode extrusion control 323, a set of substance aspiration or deployment ports 324, and an electrical energy port 325.

The handle 321 is disposed for manipulation by medical or other personnel, and can be shaped for being held in the hand.

The inflation/deflation port 322 includes a receptor for coupling to a source of air, liquid, or other flowable substance. The flowable substance inflates the treatment structure 313 when input to the inflation/deflation port 322, and deflates the treatment structure 313 when output from the inflation/deflation port 322.

The electrode extrusion control 323 includes a control element for controlling the amount of extrusion of electrodes from the treatment structure 313.

The substance aspiration or deployment ports 324 include receptors for aspirating flowable substances from or from near the treatment structure 313, and for deploying flowable substances into or near to the treatment structure 313.

The electrical energy port 325 includes a conductive element that can be coupled to a source of electrical energy, such as a battery, a generator, or a wall socket.

Treatment Device Used for Fecal Incontinence

Figure 4:
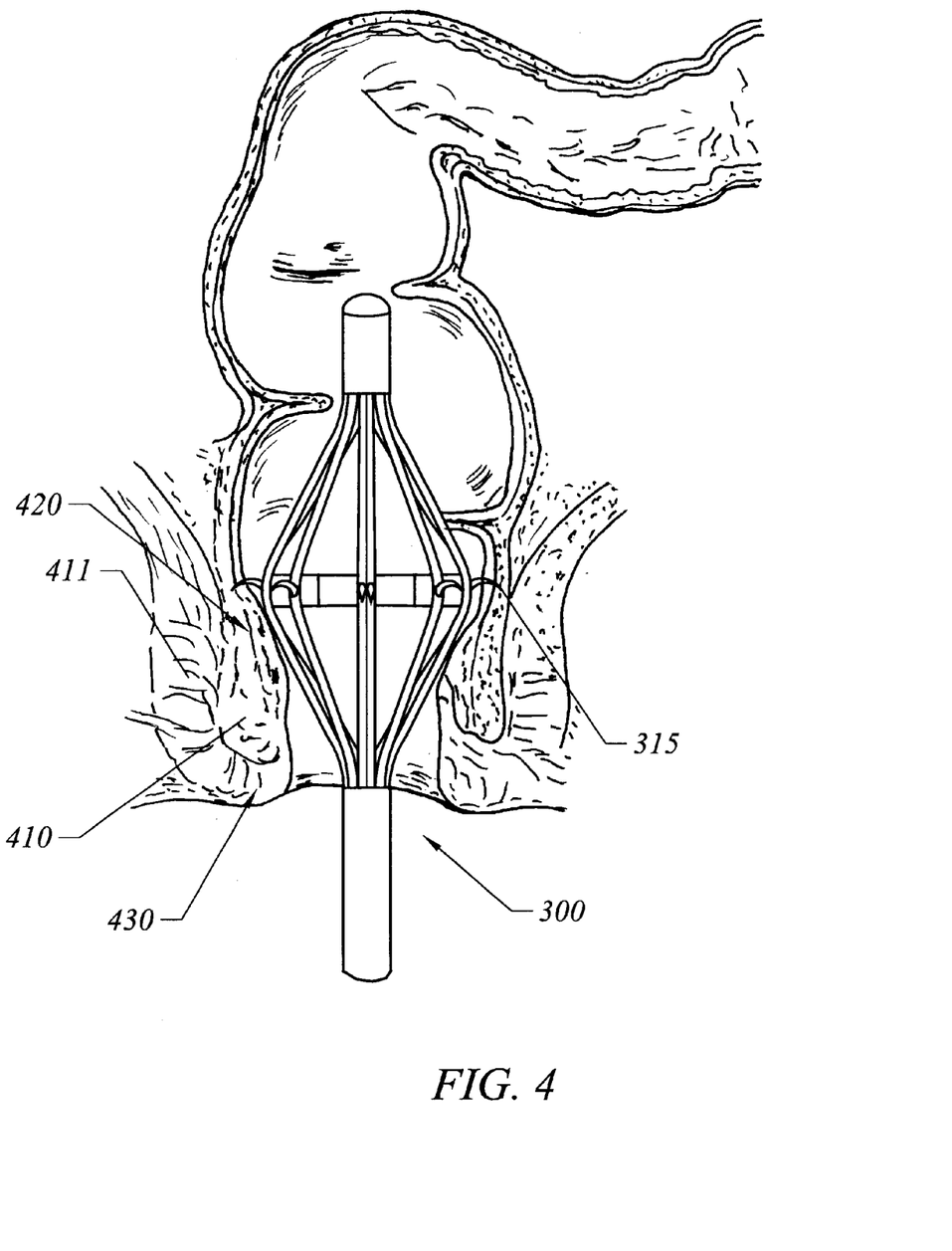
FIG. 4 shows a drawing of the second device for treatment of a body structure, as possibly positioned at or near a rectal sphincter.

FIG. 4 shows a drawing of the second device for treatment of a body structure, as possibly positioned at or near a rectal sphincter.

The device 300 is positioned at or near the rectum, preferably in a region of relatively insensate tissue 410 between the involuntary sphincter 420 and the voluntary sphincter 430.

In operation, the treatment elements 315 are extruded into the relatively insensate tissue 410. The treatment elements 315 apply pre-conditioning, treatment, and post-treatment to the relatively insensate tissue 410 and to internal tissue 411 located beneath the relatively insensate tissue 410.

The treatment elements 315 operate to perform ablation or debulking, to perform bulking or plumping, or otherwise to perform shaping or reshaping, of the relatively insensate tissue 410 and the internal tissue 411. After operation, the rectum (either the involuntary sphincter 420 or the voluntary sphincter 430 or both) are capable of a more tightly sealed closure, so as to militate against fecal incontinence.

Treatment Device Used for Urinary Incontinence

Figure 5:
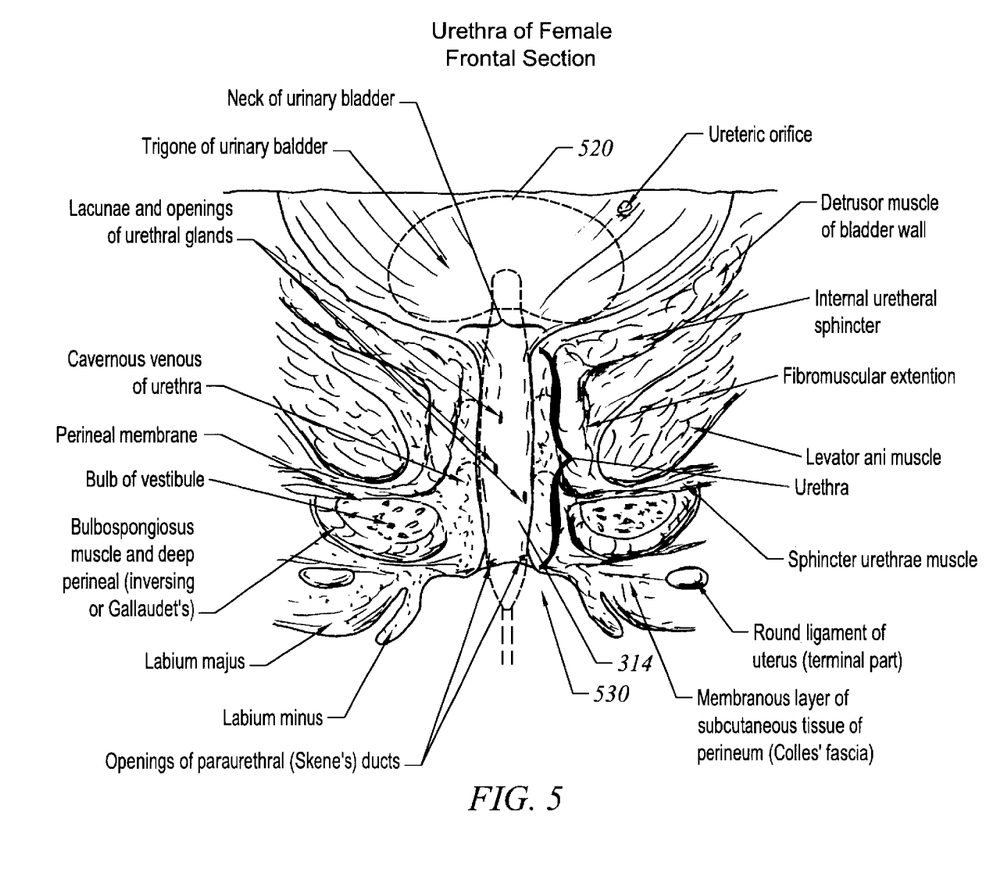
FIG. 5 shows a drawing of the second device for treatment of a body structure, as possibly positioned at or near a urinary sphincter.

FIG. 5 shows a drawing of the second device for treatment of a body structure, as possibly positioned at or near a urinary sphincter.

The device 300 is positioned at or near a urinary sphincter 510. In operation, a distal balloon (like that of the first device 100) is positioned at an exit point of the bladder 520. Inflated, the distal balloon prevents the device 300 from being mistakenly drawn out of the urethra 530.

In operation, the inflatable/deflatable structure 314 has a substantially greater length-to-width ratio, so as to fit into the urethra 530.

In operation, the treatment elements 315 are extruded into the surface of the urethra 530, and possibly into tissue there-behind. The treatment elements 315 apply pre-conditioning, treatment, and post-treatment to those tissues.

The treatment elements 315 operate to perform ablation or debulking, to perform bulking or plumping, or otherwise to perform shaping or reshaping, of those tissues. After operation, the urinary sphincter 510 and the urethra 530 are capable of a more tightly sealed closure, so as to militate against urinary incontinence.

Generality of the Invention

The invention has substantial generality of application to various fields for biopsy or treatment of medical conditions.

These various fields include, one or more of, or a combination of, any of the following (or any related fields):

As noted above, the invention can be used in any area of the body, including the biologic systems and locations noted herein. The invention can be used for the general purpose of reducing, plumping, or reshaping body structures, tissues, or regions of the body otherwise empty (or filled with biologic substances.

For examples, the invention can be used in one or more of, or some combination of, the following:

In the head and neck, such as the cheeks, eyes, throat, larynx, or other structures;

For the purpose of reforming damaged body parts, for the purpose of reshaping misshapen body parts, or for cosmetic effects; or For the purpose of replacing the volume filled by body parts that are missing, whether due to congenital defect, infection, or surgery.

Alternative Embodiments

Although preferred embodiments are disclosed herein, many variations are possible which remain within the concept, scope, and spirit of the invention, and these variations would become clear to those skilled in the art after perusal of this application.

What is claimed is:

1. An apparatus for treatment of the ingestive end of the gastro-intestinal system including
    a catheter composed of biologically nonreactive material having a distal and proximal end and a plurality of lumens running the length of the catheter, wherein said catheter is disposed for insertion into the oral cavity or a stoma;
    a distal balloon mounted circumferentially on said distal end of said catheter;
    a proximal balloon mounted circumferentially on said proximal end of said catheter; and
    a treatment element mounted upon said catheter between said distal balloon and said proximal balloon.

2. An apparatus as in claim 1, wherein said treatment element includes a circumferentially mounted balloon, including an indentation, and an electrode mounted in said indentation.

3. An apparatus as in claim 2, wherein said electrode delivers a treatment to a tissue.

4. An apparatus as in claim 3, wherein said tissue includes an esophagus.

5. An apparatus as in claim 2, wherein said indentation isolates said tissue for treatment.

6. An apparatus as in claim 1, wherein pharmaceutical agents or other liquids can be exuded from said proximal balloon so as to pre-treat a tissue.

7. An apparatus as in claim 1, wherein pharmaceutical agents or other liquids can be exuded from said distal balloon so as to pre-treat a tissue.

8. An apparatus as in claim 1, wherein pharmaceutical agents or other liquids can be exuded from said proximal balloon so as to post-treat a tissue.

9. An apparatus as in claim 1, wherein pharmaceutical agents or other liquids can be exuded from said treatment element so as to pre-treat a tissue.

10. An apparatus as in claim 1, wherein pharmaceutical agents or other liquids can be exuded from said treatment element so as to post-treat a tissue.

11. An apparatus as in claim 1, wherein pharmaceutical agents or other liquids can be exuded from a distal balloon so as to post-treat a tissue.

12. A method for treating the ingestive end of the gastro-intestinal system including the steps of:
    inserting a catheter through a mouth or stoma into an esophagus;
    isolating an area of an esophagus for treatment by placing an indentation included in a treatment element coupled to said catheter adjacent to a tissue that requires treatment, wherein said area of an esophagus requires treatment for Barrett's;
    inflating a balloon included in said treatment element;
    inflating a distal balloon so as to further isolate said tissue;
    inflating a proximal balloon so as to further isolate said tissue; and
    deploying an electrode mounted in said indentation to treat said tissue.

13. A method as in claim 12, wherein said step of inflating a distal balloon includes pre-treating a tissue with pharmaceutical agents or other liquids.

14. A method as in claim 12, wherein said step of inflating a distal balloon includes a post-treating said tissue with pharmacuetical agents or other liquids.

15. A method as inc claim 12, wherein said step of inflating a proximal balloon includes steps for pre-treating said tissue with pharmaceutical agents or other liquids.

16. A method as in claim 12, wherein said step of inflating a proximal balloon includes steps for post treating said tissue with pharmaceutical agents or other liquids.

17. A method as in claim 12, wherein said step of deploying an electrode includes exuding an electrolytic solution.

18. A method as in claim 12, wherein said step of deploying an electrode includes emitting RF energy into said tissue.

* * * * *